(12) United States Patent
Johnsen

(10) Patent No.: US 8,502,974 B2
(45) Date of Patent: Aug. 6, 2013

(54) UNDERWATER HYPERSPECTRAL IMAGING (75) Inventor: Geir Johnsen, Trondheim (NO)

(73) Assignee: Ecotone AS, Trondheim (NO)

(*) Notice: Subject to any disclaimer, the term of this patent is extended or adjusted under 35 U.S.C. 154(b) by 210 days.

(21) Appl. No.: 12/994,091

(22) PCT Filed: May 21, 2009

(86) PCT No.: PCT/GB2009/001288
§ 371 (c)(1),
(2), (4) Date: Feb. 25, 2011

(87) PCT Pub. No.: WO2009/141622
PCT Pub. Date: Nov. 26, 2009

(65) Prior Publication Data
US 2011/0205536 A1    Aug. 25, 2011

(30) Foreign Application Priority Data
May 21, 2008  (GB) ................... 0809252.0

(51) Int. Cl.
*G01J 3/28* (2006.01)
*G01J 3/40* (2006.01)
*H04N 9/47* (2006.01)
*H04N 7/18* (2006.01)

(52) U.S. Cl.
USPC ............ 356/326; 356/303; 348/81; 348/148

(58) Field of Classification Search
USPC ................ 356/326, 303; 348/81, 148
See application file for complete search history.

(56) References Cited

U.S. PATENT DOCUMENTS

| | | | |
|---|---|---|---|
| 6,028,663 A * | 2/2000 | O'Mongain et al. | 356/213 |
| 6,490,075 B1 * | 12/2002 | Scheps et al. | 359/285 |
| 7,417,666 B2 * | 8/2008 | Kaltenbacher et al. | 348/81 |
| 7,433,026 B2 * | 10/2008 | Wolpert et al. | 356/39 |
| 8,194,125 B2 * | 6/2012 | Mack et al. | 348/131 |
| 2007/0203623 A1 * | 8/2007 | Saunders et al. | 701/23 |

FOREIGN PATENT DOCUMENTS

| | | |
|---|---|---|
| CA | 2547359 A1 | 6/2005 |
| GB | 2403615 A | 1/2005 |
| WO | WO0109623 | 2/2001 |
| WO | WO0177627 | 10/2001 |
| WO | WO2005076736 | 8/2005 |

OTHER PUBLICATIONS

Heather Holden, Ellsworth LeDrew, "Measuring and modeling water column effects on hyperspectral reflectance in a coral reef environment", Aug. 2002, Remote Sensing of Environment, vol. 81, Issues 2-3, pp. 300-308.*
Chang, Grace et al., "The New Age of Hyperspectral Oceanography." Oceanography Jun. 2004; 23-29.
Volent, Isolt et al., "Kelp Forest Mapping by Use of Airborne Hyperspectral Imager." *Journal of Applied Remote Sensing* vol. 1, 011503 (2007):1-21.
Sigernes, Fred, Dag Arne Lorentzen, Karsten Heia, and Trond Svenøe. "Multipurpose Spectral Imager." Applied Optics 39.18 (2000): 3143-3153.

* cited by examiner

*Primary Examiner* — Gregory J Toatley
*Assistant Examiner* — Sahwn Decenzo
(74) *Attorney, Agent, or Firm* — Koppel, Patrick, Heybl & Philpott (57) ABSTRACT

An apparatus for placement on or in a body of water for hyperspectral imaging of material in the water comprises an artificial light source and a hyperspectral imager. These are arranged so that in use light exits the apparatus beneath the surface of the water and is reflected by said material before re-entering the apparatus beneath the surface of the water and entering the hyperspectral imager. The hyperspectral imager is adapted to produce hyperspectral image data having at least two spatial dimensions.

36 Claims, 5 Drawing Sheets

UNDERWATER HYPERSPECTRAL IMAGING

This is a National Stage Application of PCT/GB2009/001288 filed May 21, 2009, published as WO 2009/141622 A1, and claiming priority from GB0809252.0 filed May 21, 2008.

FIELD OF INVENTION

This invention relates to hyperspectral imaging of aquatic specimens and scenes.

BACKGROUND OF THE INVENTION

When viewing a scene using a traditional digital imaging sensor or by eye, the intensity of light from each point or pixel of the imaged scene can be determined for each of three wavelength bands (centred around red, green and blue for a digital camera, and yellowish-green, green and bluish-violet for the human eye). Information about the full spectral emissions (i.e. a continuous graph of intensity over wavelength) of the scene can, at best, be represented in only a three-dimension colour space, necessitating a loss of information.

Multispectral sensors have been used in research into aquatic (freshwater, brackish water and salt water) environments for about 30 years. Multispectral sensors are divided into more than three discrete colour bands and so give more detailed spectral information. They typically have a minimum wavelength resolution of 10 nm. They have typically been carried in satellites, aeroplanes, buoys and boats to analyse upwelling radiance remotely, and in underwater vehicles to measure both upwelling and downwelling radiance in situ. In both cases the light measured by the sensor comes from natural illumination that is incident on the water.

Hyperspectral sensors are also known. These have a much better wavelength resolution than multispectral sensors—at least 10 nm or better and can operate over a broad range of wavelengths including visible light and typically also into ultraviolet and infrared frequencies. It is also known to use hyperspectral sensors for imaging purposes in passive remote sensing. A hyperspectral imager (also known as an imaging spectrometer, imaging spectroscope, imaging spectroradiometer, superspectral or ultraspectral imager), is capable of determining the light intensity from each point or pixel of a scene for each of a large number (typically hundreds) of wavelength bands, each no more than 10 nm wide. This results in far more spectral information about the scene being preserved than is the case when just three bands are available, as for conventional imaging.

Because hyperspectral imagers give such detailed spectral information for each pixel in the image, independently of each other, it is possible to identify regions containing particular types of matter, such as chemical substances and organisms, by using their known unique spectra.

Applications for hyperspectral imagers include mineral exploration, agriculture, astronomy and environmental monitoring. They are typically used in aeroplanes (so-called "remote" viewing).

An overview of the use of hyperspectral sensors in oceanography is given is "The New Age of Hyperspectral Oceanography" by Chang et al. in *Oceanography*, June 2004, pp. 23-29. WO 2005/054799 discloses the use of a hyperspectral imager from airborne platforms to observe coastal marine environments remotely. The use of an airborne hyperspectral imager for mapping kelp forest distribution close to the shore is described in "Kelp forest mapping by use of airborne hyperspectral imager" by Volent et al. in *Journal of Applied Remote Sensing*, Vol. 1, 011503 (2007).

However, the applicant has realised that taking hyperspectral images remotely from the air or from space has several limitations. For example, even for very optically clear water, such as can be found in the Arctic, it is not possible to distinguish features of the sea bottom or of suspended matter beyond a depth of a few meters. In more typical marine waters, even this limited visibility is drastically reduced and is normally less than a meter or so—in murkier waters maybe only a few centimeters might be penetrable by light. This limits the usefulness of this technique. Additional problems occur due to interference from the air between the water surface and the remote imager; for example, due to clouds and to Rayleigh scattering. It is also necessary to take into account the angle of the sun in the sky.

BRIEF SUMMARY OF THE INVENTION

Furthermore, the spatial resolution of conventional remote sensing systems, such as a hyperspectral imager mounted in an aeroplane, is typically relatively low.

When viewed from a first aspect the invention provides an apparatus for placement on or in a body of water for hyperspectral imaging of material in the water comprising an artificial light source and a hyperspectral imager which are arranged so that in use light exits the apparatus beneath the surface of the water and is reflected by said material before re-entering the apparatus beneath the surface of the water and entering said hyperspectral imager, wherein said hyperspectral imager is adapted to produce hyperspectral image data having at least two spatial dimensions.

In accordance with the invention there is provided a new method and apparatus for aquatic hyperspectral imaging (optical measurements by using artificial light sources) which open up the possibility for wider and more accurate uses of hyperspectral imagers in underwater environments. Two-dimensional hyperspectral images of underwater material can be obtained from in situ apparatus; i.e. apparatus that is at least partially submerged. By having control of the light source, more accurate measurements of reflectance and transmission characteristics can be made, since there is no need to calibrate for solar angle above the horizon, and there are no atmospheric distortions to worry about. Moreover hyperspectral imaging can be carried out at any depth, rather than just at the surface as with remote sensing approaches.

Moreover by carrying its own artificial light source, the apparatus can be used to image material at much greater depths; either because it can be made bright enough to penetrate further, or because the apparatus itself can be submerged to the required depth. A further advantage given by the on-board light source is that the emission spectrum of the light source can be chosen or tailored to the reflectance spectrum of the material being looked for or expected and the optical properties of the water. These optical properties are affected by coloured dissolved organic matter, suspended matter, phytoplankton etc. Thus if a particular material is being searched for, the light source can be chosen to ensure that it is illuminated by all the desired wavelengths corresponding to peaks in its reflection spectrum. Equally the appropriate light source can be chosen absorption and scattering properties of the water in which the unit is operating can be For example an apparatus in accordance with the invention, such as an autonomous underwater vehicle (AUV), remotely operated vehicle (ROV), could be provided with a plurality of light sources. Each light source could be used in different conditions or when looking for different materials; or indeed they could be blended together in varying proportions to give further lighting options.

Indeed in a set of preferred embodiments the apparatus comprises means for adjusting the spectrum of light emitted by the light source or by a plurality of light source. This allows the possibility of "tuning" the overall spectral output of the light source(s) as needed. This could be an adjustment made for each mission or could be adjusted dynamically—either manually or under programmed or feedback control. For example a calibration surface having known reflectance characteristics could be deployed and feedback control used to alter the output spectrum depending on the spectrum of the light reflected from the calibration surface until a desired spectrum is achieved. A non-limiting example of such a calibration surface is a white Teflon® (polytetrafluoroethylene) disc deployed in front of the hyperspectral imager at a given distance.

The hyperspectral imager could though be calibrated using other instruments such as a (non-imaging) spectroradiometer, spectrophotometer or a spectrofluorometer. The apparatus may comprise further instruments such as a spectrophotometer, a spectrofluorometer, an acoustic Doppler current profiler (ADCP), a chlorophyll fluorescence sensor (passive Ch1 a fluorometer (no artificial excitation light source), blue excitation light stimulated Ch1 a fluorometer or LED laser Ch1a fluorometer), a coloured dissolved organic matter (cDOM) sensor, a backscattering meter, a turbidity meter, a temperature sensor or a salinity meter. Determinations from these other instruments may be used to adjust the output of the hyperspectral imager and/or the light source.

In one example the spectrum adjusting means could comprise one or more optical filters selectably placeable in the path of the emitted light. Preferably more than one filter is available, each filter having a unique spectral-filtering characteristic. Alternatively or additionally the light source may comprise a plurality of light-emitting elements each with differing emission spectra, the spectrum adjusting means comprising means for altering the power supplied to respective elements in order to give a required overall output spectrum. The light emitting elements could comprise light emitting diodes (LEDs). The LEDs could emit light substantially at a single-frequency—e.g. red, green or blue light—or could contain phosphors that emit light across a range of frequencies—e.g. white light. A mixture of coloured and white LEDs could be employed.

It is important to note that the present invention is not concerned with simple hyperspectrometers (e.g. spectroradiometers) providing a spectral analysis of effectively a single light beam travelling along a single path. A hyperspectral imager on the other hand can produce a two-dimensional representation of a scene containing hyperspectral information for each of many points across the scene.

The addition of spatial dimension information over simple hyperspectral sensor output data, allows hyperspectral imagers to be used in a wide variety of applications. In general it allows the identification of underwater material of interest in situ in an aquatic environment (bio-geo-chemistry). This can have many useful applications such as enhanced environmental monitoring; developing theme-maps of materials of interest that are geolocalized and have a time tag; creating a time-series of hyperspectral images of a region including a given material of interest; monitoring and surveillance of materials of interests in a given region; identification of unusual activities (e.g. mass occurrence of a given organism, planktonic or benthic; oil leakage; leakage of other minerals/chemicals; metal disintegration).

The hyperspectral imager could, for example, use dispersive spectrography (DS), Fourier transform spectrography (FTS) or Hadamard transform spectrography (HTS). Dispersive spectrography generates a spectrum by optically dispersing incoming radiation according to its spectral components while FTS and HTS use the Michelson interferometer principle to generate a spectrum by modulating incoming radiation in the time domain through interference by use of moving mirrors or a Hadamard array respectively; the modulated radiation in the time domain is then Fourier transformed into spectral components. Preferably the imager uses dispersive spectrography; this reduces the need for moving parts and permits a compact, robust and low-cost construction with relatively low power consumption, and good resistance to the low temperatures that may be experienced underwater. Preferably the imager operates using the push-broom technique. Preferably movement of the whole apparatus (e.g. forward motion of an underwater vehicle) enables an area of interest to be continuously imaged; this contrasts with FTS and HTS approaches in which separate, discrete images would need to be formed and then assembled to image a large area. Preferably it has no independently moving parts; this contrast with FTS which requires a moving mirror and HTS which requires a moving grating or mask.

The apparatus could be tethered to a ship or other vessel. Such a tether could comprise an umbilical power supply. Alternatively and preferably the apparatus could move independently; e.g. it might comprise a portable power supply such as batteries or means for generating its own power. Whether tethered or untethered, control of the apparatus could be exercised from a support vessel, or even from land, or the apparatus could be completely autonomous. In some preferred embodiments the apparatus is not physically connected to any above-surface apparatus, and comprises a battery power supply, which may be lead-acid or nickel-based, but is preferably lithium-based so as to be relatively compact and light-weight. Alternatively or additionally, the apparatus may comprise any other suitable power supply such as a combustion engine, a nuclear reactor, or a capacitor (e.g. a super capacitors).

The apparatus preferably comprises image capture means, such as a digital video camera, for capturing frames from the hyperspectral imager for subsequent analysis; it may additionally or alternatively comprise image processing means arranged to process captured images from the hyperspectral imager; it may, for example, be arranged to compile time-sequential frames into a representation of a scene.

The apparatus could be a floating vessel. In a set of preferred embodiments however it is adapted to be fully submersible. Embodiments of the invention comprise a housing made substantially of metal, e.g. aluminium or marine steel. In a preferred set of embodiments part of the housing or hull is transparent to permit the exit and entrance of light from/to the light source and imager. For example it could comprise one or more transparent panels, e.g. made of soda glass, quartz, acrylic glass or other suitable material. In some embodiments, the entire housing could be constructed of transparent material.

Alternatively the light source and/or hyperspectral imager (or at least an optical part thereof) could be provided in a separate pod attached to the rest of the vessel.

The housing is advantageously designed to withstand external pressures of at least 2 bars; preferably at least 10 bars; and possibly at least 100 bars. In some embodiments where a vessel in accordance with the invention is required to be used in the very deepest parts of the ocean it may be necessary for the housing to withstand pressures of the order of 1000 bars.

The invention also extends to a method of generating hyperspectral images. When viewed from a further aspect, the invention provides a method of imaging material beneath the surface of a body of water comprising:

illuminating said material with an artificial light source from beneath the surface of the water;

receiving from beneath the surface of the water light reflected from said material into a hyperspectral imager; and said imager generating hyperspectral image data from said material, said image data having at least two spatial dimensions.

Preferably the apparatus is as described in accordance with the first aspect of the invention. Preferably the artificial light source is provided in the same unit, such as a vessel or underwater platform, as the imager. It is envisaged however that it could be provided on an attached unit, or even a separate, unconnected unit.

In a set of embodiments the method comprises the further step of adjusting the output spectrum of the artificial light source. In some embodiments the hyperspectral imager is used to determine whether a desired spectrum for the artificial light is achieved. The method may comprise the further step of locating a spectral filter in the path of the artificial light; it may also or instead comprise the step of selectively illuminating elements from among a set of spectrally-distinct light-emitting elements.

In a set of preferred embodiments the apparatus is used to locate or map the extent of one or more organisms or other material by the characteristic spectral fingerprint(s) thereof. However this relies on these spectral fingerprints being known. The spectral fingerprints might be obtainable from an existing library, database or other source. However in a preferred set of embodiments a library is built up or extended by using a hyperspectral imager to obtain a spectral profile of a specimen (object of interest). That specimen can be identified by other means—e.g. visually by an expert or by independent analysis—and the profile associated with the identity of the material. In some preferred embodiments, a combination of analysis methods are used to build up the database; especially preferred is to use a hyperspectral imager in combination with high-precision liquid chromatography (HPLC) and/or liquid-chromatography mass spectrometry (LC-MS). These latter techniques are preferably used to isolate and characterise a substance (e.g. molecules) that contributes to an optical signature for a specimen. For example, HPLC may be used to characterise optically different types of chlorophylls and/or carotenoids.

This is considered to be novel and inventive in its own right and thus when viewed from a further aspect, the invention also provides a method of identifying an underwater material comprising:

analysing a specimen of a material extracted from a body of water using a hyperspectral imager to determine a hyperspectral profile of said material and storing said hyperspectral profile;

taking an image of an underwater scene in a body of water using said hyperspectral imager or a further hyperspectral imager;

generating an observed hyperspectral profile from said scene; and comparing said observed hyperspectral profile with said stored hyperspectral profile to identify said material and recording a positive identification if the comparison is sufficiently close.

Thus it will be seen by the person skilled in the art that underwater material can be identified based on a prior analysis of a sample of that material. The specimen may, for example, be a mineral; a protein; a pigment; oil; a metal (e.g. copper, iron); disintegrating metal (e.g. rust); a bacterium; a eukaryote; a marine invertebrate; a marine vertebrate; microphytobenthos; macrobenthos; a benthic filter feeder; a phytoplankton; a zooplankton; a larva; a fish; kelp; an alga; sediment; a biological mat (bacteria and microscopic eukaryotes covering sediments); a hydrocarbon; vegetation; wood; an artefact (e.g. a ship-wreck or a lost item); a hydrothermal vent; a cold seep; or a plurality, or any combination, of the above.

Imaging may be conducted near the water surface, within the water column or on the bottom, both for marine and fresh water.

Once reflectance, R(lamda), and/or transmission, T(lamda) (where lamda is the wavelength of light) characteristics are obtained for an object of interest, preferably embedded in water to mimic natural conditions, this information can further be used to calibrate and compensate for the effects of optical path length in water masses of different types (e.g. case I and II waters where the content of phytoplankton, coloured dissolved organic matter and suspended matter needs top be adjusted for since they will alter the spectral characteristics of the emitted light to the hyperspectral imager due to different spectral attenuation coefficients, K(lambda), in the water).

Measurements of R(lamda) from a given object of interest made under controlled conditions may be used to adjust for the optical path length (distance from the light source to the object and back to the hyperspectral imager) and/or to determine optical characteristics of the intervening water.

Preferably the apparatus comprises an optical sensor and means for estimating a spectral attenuation coefficient of the ambient water using an output from said optical sensor. Preferably such estimations are made continually or continuously. Preferably these estimations are used to adjust the output of the artificial light source; e.g. to tune the spectral output of one or more lamps (LED, halogen, HID, etc.) so that a predetermined light spectrum will be received at a target object and/or to compensate for the attenuation of reflected or emitted light returning to the apparatus. The predetermined light spectrum may be a substantially uniform energy across the visible spectrum e.g. 400-700 nm (i.e. white light), or it may be of any other appropriate shape.

Preferably the method comprises the step of storing said hyperspectral profile in a database of hyperspectral profiles. Preferably the method then also comprises the step of retrieving the hyperspectral profile from the database. This allows, for example, entirely new chemical species and/or biological entities, previously unknown to man, to be highlighted as they will not be found to be in the database of known substances. Such discoveries may have applications to the food, energy and pharmaceutical industries (e.g. bio-prospecting), among others.

Preferably the same hyperspectral imager, or one with the same optical characteristics is used. In this way, no correction for optical artefacts unique to a particular imager is required.

Preferably the step of taking an image of an underwater scene comprises use of apparatus according to the first aspect of the invention.

Data are preferably stored on a hard disk. Analysis of the data may be performed; e.g. discriminant analysis, principal component analysis, standard error of replicate measurements, or mean coefficient of variation. The step of recording a positive identification could comprise displaying on a display or storing in a volatile or non-volatile memory or other digital data storage medium.

Preferably the step of analysing comprises using the hyperspectral imager in an apparatus comprising an objective lens, e.g. by coupling the hyperspectral imager to a microscope. Preferably the specimen is submerged in liquid, preferably water, preferably seawater. Many materials and objects, including aquatic specimens such as algae, have different spectral characteristics when they are in water compared with in air. There are therefore significant advantages in analysing them in a liquid.

It will be appreciated that, in addition to having advantageous optical effects (e.g. no reflected light from light source, imitating the spectral characteristics of the object of interest in situ under controlled conditions in the laboratory), the apparatus of this aspect of the invention allows controlled measurements in the laboratory of marine organisms of different taxa to be taken in vivo (i.e. with the specimen alive and in good shape). Nonetheless, it may be desirable on occasions to generate hyperspectral images of specimens that are dead or decaying.

The apparatus may further comprise additional means for determining in vivo spectral absorption or fluorescence excitation spectra; or for performing high precision liquid chromatography (HPLC), liquid chromatography mass spectrometry (LC-MS), or nuclear magnetic resonance spectroscopy (NMR). These additional means may facilitate the isolation, identification, characterisation and quantification of entities such as pigments or other bio-molecules or bio-active molecules; this information may subsequently be used for in situ underwater bio-prospecting of substances of interests (e.g. bioactive substances). It may thereby be possible in situ to identify an object of interest and also to determine its optically-active chemical composition.

For example, a mat of cyanobacteria on a seafloor may give an hyperspectral image reflectance drop at 440, 490, 545 and 680 nm. From previous HPLC analysis it is known that the 440 and 680 nm peaks are related to the absorption peaks of Ch1 a; the 490 nm peak corresponds to zeaxanthin; and the 545 nm peak corresponds to phycoerythrin. If some of the pigments were unknown, subsequent analysis could be performed using LC-MS to find the molecular weight of the given compound; this would allow it to be characterised and added to the database.

This is considered to be novel and inventive in its own right and thus when viewed from a further aspect, the invention also provides a method of identifying an underwater material comprising:

taking an image of an underwater scene in a body of water using a hyperspectral imager;
generating an observed hyperspectral profile from said scene; and
using a database to compare said observed hyperspectral profile with a stored optical profile to identify a molecule and recording a positive identification of that molecule in the scene if the comparison is sufficiently close.

The molecule may be a pigment such as a chlorophyll, carotenoid, phycobiliprotein or axylene. Preferably a plurality of different molecules are identified in the scene and preferably the method further comprises the step of identifying said material from said identification of the molecule(s).

In any of the foregoing aspects, the hyperspectral imaging component is preferably arranged to distinguish between wavelengths to a resolution finer than 10 nm; more preferably between 0.5 and 2 nm; and most preferably finer than 1 nm; e.g. 0.5 run. Advantageously, the spectral resolution of the imaging component is adjustable; preferably while the apparatus is deployed. Thus the spectral resolution can be set to match the prevailing conditions, noting that the signal-to-noise ratio may be improved if the spectral resolution is made coarser. For example in murky waters or when imaging far-away objects, the spectral resolution may be made coarser to, say, between 5 and 10 nm, so as to enhance the signal-to-noise ratio (at the expense of spectral resolution). The hyperspectral imaging component is preferably arranged to image over the whole spectrum of visible light; e.g. 400-700 nm. It may alternatively or additionally be arranged to image outside the visible spectrum; e.g. at wavelengths below 400 nm and/or above 700 nm.

The hyperspectral imaging component preferably has a maximum dimension less than 1 meter and more preferably less than 50 cm; e.g. between 20 and 30 cm. Preferably it has a second-largest dimension less than 50 cm; more preferably less than 10 cm; e.g. approximately 5 cm. The person skilled in the art will appreciate that this is considerably smaller than many previous hyperspectral imagers; this allows the present imaging component to fit into commercially-available UUVs, AUVs, underwater gliders and ROVs.

The hyperspectral imaging component of the present invention is preferably also under 5 kg in weight; more preferably under 1 kg; e.g. between 500 and 1000 g. It preferably has a power consumption of less than 10 W; more preferably less than 5 W; most preferably less than 2 W.

When viewed from another aspect the invention provides an apparatus for imaging a specimen comprising an objective lens, a hyperspectral imager in optical communication with said lens, a vessel suitable for holding a specimen in liquid such that at least a part of said specimen is situated in the focal plane of said lens.

The invention extends to a method of imaging a specimen immersed in liquid in a container using a hyperspectral imager.

Thus it will be seen that an apparatus is provided which may be used in a laboratory situation to analyse samples in a fluid using a hyperspectral imager. As above preferably the liquid is water such as seawater.

The specimen could be static during the analysis. Preferably however the apparatus comprises means operable to move said vessel relative to said lens in a direction parallel to said focal plane. This allows a hyperspectral image with two spatial dimensions to be built up. This might be useful for example in establishing an area of an object comprising a certain material and obtaining an averaged hyperspectral profile across that area. Thus a preferred method comprises moving the specimen relative to an objective lens of said imager in a direction parallel to the focal plane of the lens and forming a two-dimensional image of the specimen.

Preferably the apparatus comprises an artificial light source e.g. a halogen, xenon, metal halide (HID, light arc) lamp. The advantages of an artificial light source are discussed above in relation to the first aspect of the invention. Light from the light source may be directed onto or through the specimen by optical diffusers, optical fibres and/or mirrors. The apparatus may be arranged to generate images using light reflected from the specimen, or light transmitted through the specimen, or both.

There may be an air gap between the front of the objective lens and the surface of the fluid, but preferably the objective lens is at least partially immersed in the fluid. Thus optical interference due to the light passing through air between the fluid surface and the objective lens is avoided.

Preferably this method uses apparatus as set out in the preceding aspect of the invention.

Various aspects and features of the invention have been set out above. Features described with reference to one aspect should not be understood as being limited to that aspect only, but rather as also being applicable to any of the other aspects where appropriate.

Certain preferred embodiments of the invention will now be described, by way of example only, with reference to the accompanying drawings, in which.

BRIEF DESCRIPTION OF THE DRAWINGS

DETAILED DESCRIPTION OF INVENTION

Figure 1:
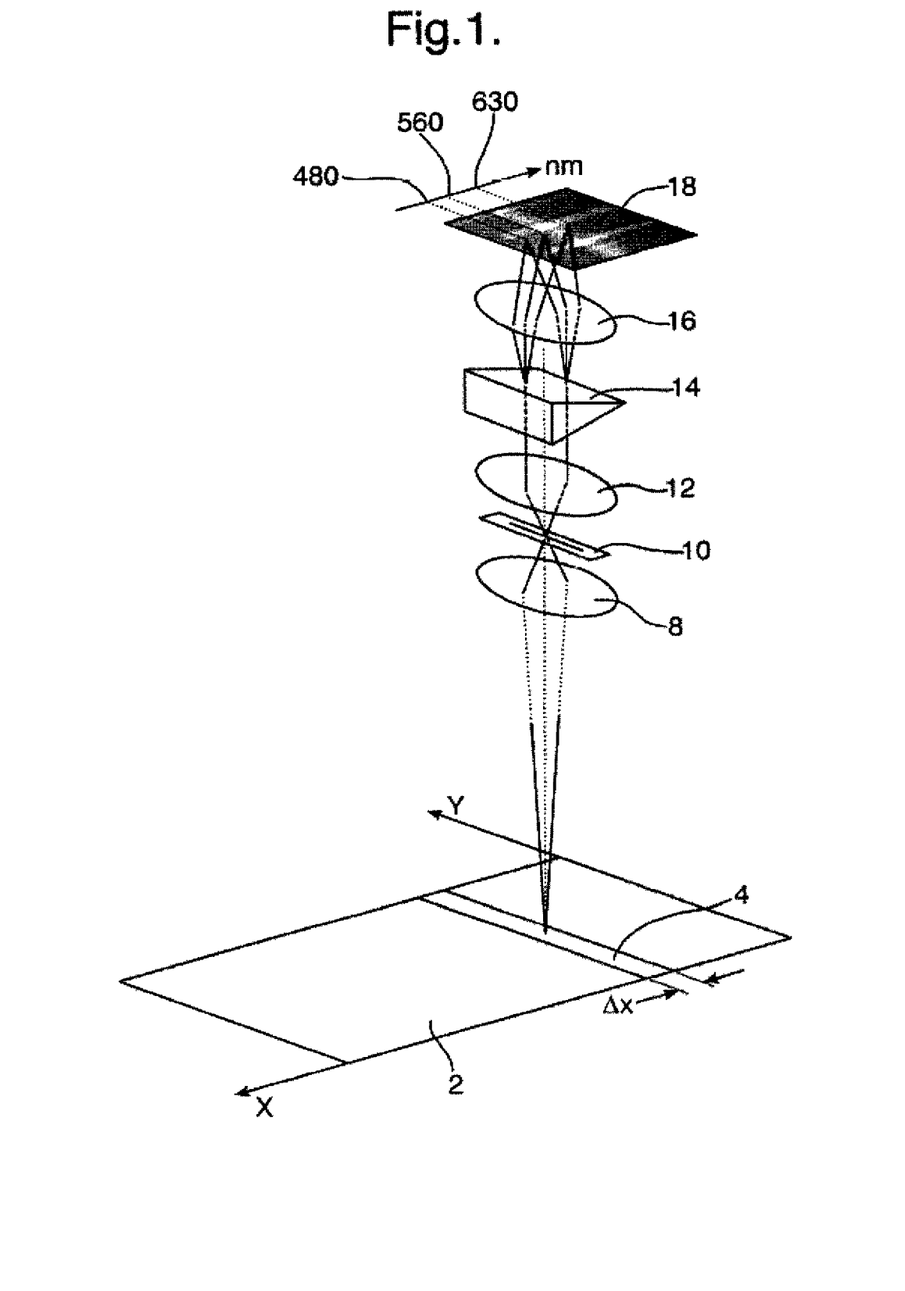
FIG. 1 is a schematic, perspective drawing of the principle components of a hyperspectral imager as used in embodiments of the invention.

First an example of the use of a hyperspectral imager to form an image having two spatial dimensions will be described with reference to FIG. 1. FIG. 1 shows how light passes from a scene 2 through the optics of a push-broom hyperspectral imager during the capture of a single frame. Only a thin strip 4 of the scene is imaged during each time frame, extending in the direction of the Y axis and having width ΔX. Light from the scene first passes through an objective lens 8 which focuses it through an entrance slit 10. The slit excludes light other than that emanating from the strip 4. Its width is set to relate desired width ΔX to the width of a single row of pixels of a CCD image sensor 18. A collector lens 12 then directs light through a grism 14, which is a combination of a grating and a prism arranged to create a dispersed spectrum. The spectral dispersion occurs over the X axis, orthogonal to the spatial dimension Y of the strip 4. A camera lens 16 then focuses the spectrally dispersed light onto a CCD image sensor 18.

In order to build up an image of a two-dimensional scene, the objective lens 8 and other optics are, over time, moved laterally relative to the scene 2 in the direction of the X axis. The speed of motion is determined such that each sequential frame captures a strip 4 of the scene along the Y axis immediately adjacent the preceding strip. The sequential frames can be processed and composed to generate a hypercube. If desired, this hypercube can be used to generate two-dimensional flat greyscale images indicating light intensity at each pixel for a given single optical wavelength range. The wavelength resolution of the apparatus is determined by the number of pixels on the CCD sensor 18 in the direction of the X axis.

Figure 2:
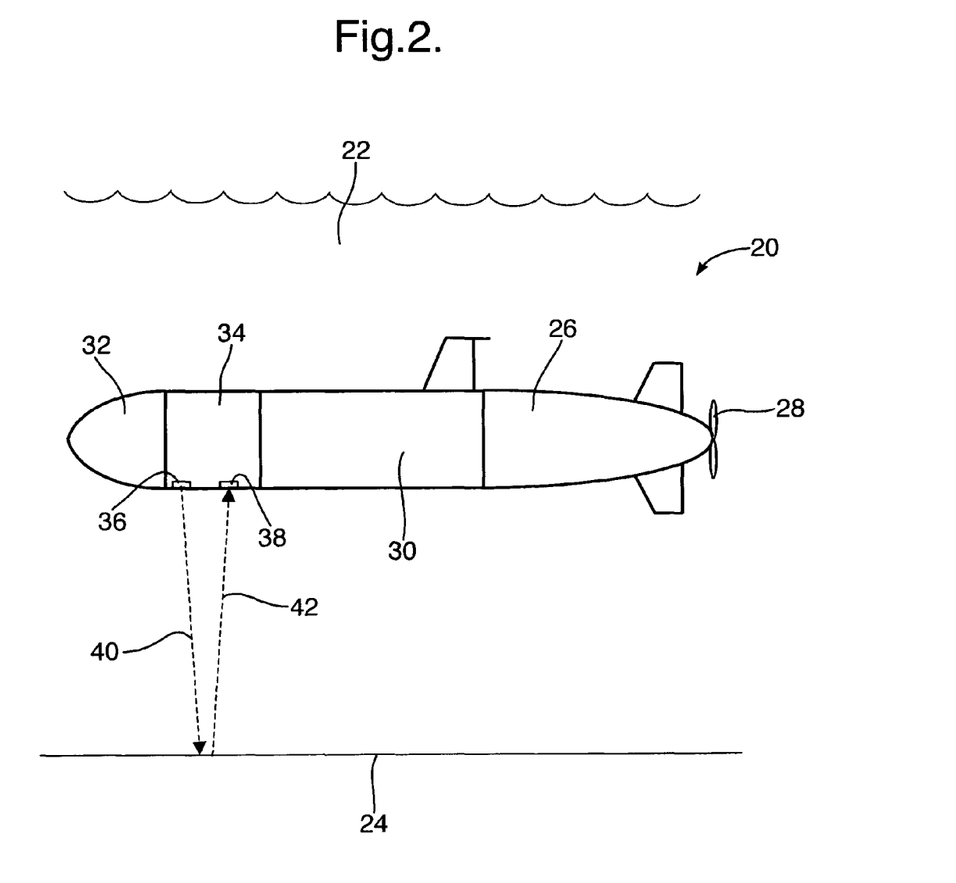
FIG. 2 is figurative diagram showing a vertical cross-section through an underwater vehicle embodying the invention.

FIG. 2 shows an autonomous underwater vehicle (AUV) 20 according to an embodiment of the invention in a body of water 22 above a seabed 24. A suitable AUV is the REMUS developed by the Woods Hole Oceanographic Institution. The AUV 20 comprises a tail section 26 containing the propulsion motor and controller circuitry for a propeller 28. A mid-body section 30 houses various operational components of the vehicle. Between the mid-body section 30 and a nose cone 32 is an optics section 34. The optics section 34 comprises a watertight chamber carrying a hyperspectral imager and a light source (not shown). A transparent outlet window 36 allows light 40 from the light source to emerge towards a scene of interest, such as the seabed 24. Light 42 returning from the scene enters through a transparent inlet window 38 behind which is located the objective lens 8 of a hyperspectral imager.

Figure 3:
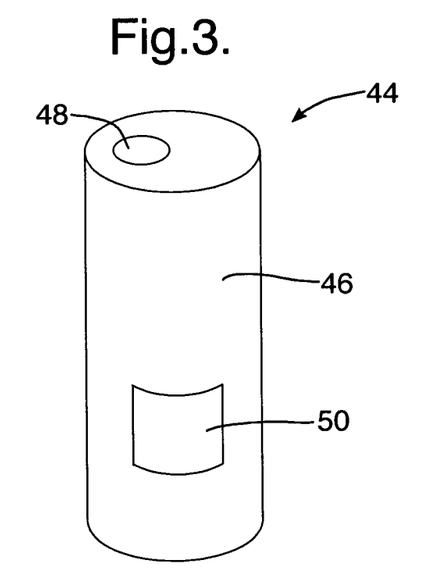
FIG. 3 is a perspective drawing of the exterior of an underwater hyperspectral imager embodying the invention.

FIG. 3 shows another embodiment of an underwater apparatus 44 embodying the invention. This apparatus 44 is not self-propelling but rather can be lowered into the water attached to a floater and so be immersed in the water for towing by a boat for example, or carried by a human diver. It comprises a watertight housing 46 made of aluminium or marine steel having a transparent window 48 made of soda glass or quartz to allow the passage of light into, and optionally out of, the imager 44. It also has a display panel 50 for turning the system on and off, tuning the frame, gain, iris and gamma controls. Inside the housing 46, there is a hyperspectral imager, batteries and video recorder and there may be one or more lamps. The apparatus 44 may also carry external underwater lamps (not shown) such as an Underwater Kinetics Light Cannon 100, which can be used to obtain 6000 degrees Kelvin colour temperature. The imager can be used in any orientation; i.e. it can be pointed horizontally, up or down.

In both cases above the apparatus could carry several lamps which can be used individually or in combination to provide a customised illumination. This can be used to minimise the effects of absorption and scattering in the water between the light source, imaged material and the imager, and can also ensure that the correct wavelengths in the imaged material are excited.

Figure 4:
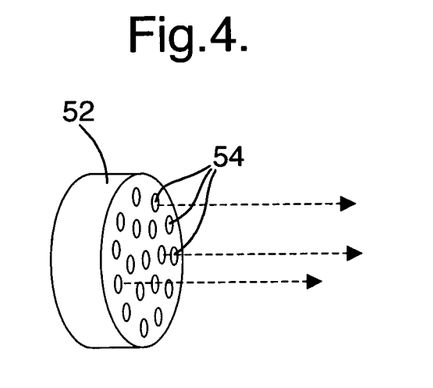
FIG. 4 is a perspective drawing of a light source for use with embodiments of the invention.

The lamp 52 shown in FIG. 4 is also suitable for use with imagers embodying the invention, such as those of FIGS. 2 and 3 and takes the idea of blending light sources one step further. The lamp 52 comprises a plurality of light emitting diode (LED) lamps 54 which can be selectively illuminated. Some of the LEDs are white, emitting light in the range 350-800 nm. Others are blue (emitting light in 400-500 nm range), green (500-600 nm), and red (600-700 nm).

The spectrum of light emanating from the lamp 52 can be tuned by selecting which LEDs to activate, depending on the optical properties of the water (which vary with distance to the target object due to the spectral attenuation coefficient of water, and which can vary due to optically-active components such as phytoplankton, coloured dissolved organic matter and total suspended matter).

Either of the two underwater apparatus described above can be used to capture and record two-dimensional hyperspectral images beneath the water. By carrying its own artificial light source, the imaging apparatus can measure much more accurate hyperspectral information than is possible using airborne remote sensing. For example the effects of solar horizontal, and of atmospheric scattering and distortion are removed. Moreover the path length of the emitted and reflected light through the water can be relatively short, whatever depth the imaged material is at.

One application of the principles of the invention is in mapping or prospecting for materials by using a database of spectral profiles that correspond to known materials such as particular compounds, substances or organisms to compare against the spectral profiles measured from the captured images. The spectral profiles on the database might be commercially or publicly available. However below a method of building up or adding to such a database will be described.

Figure 5:
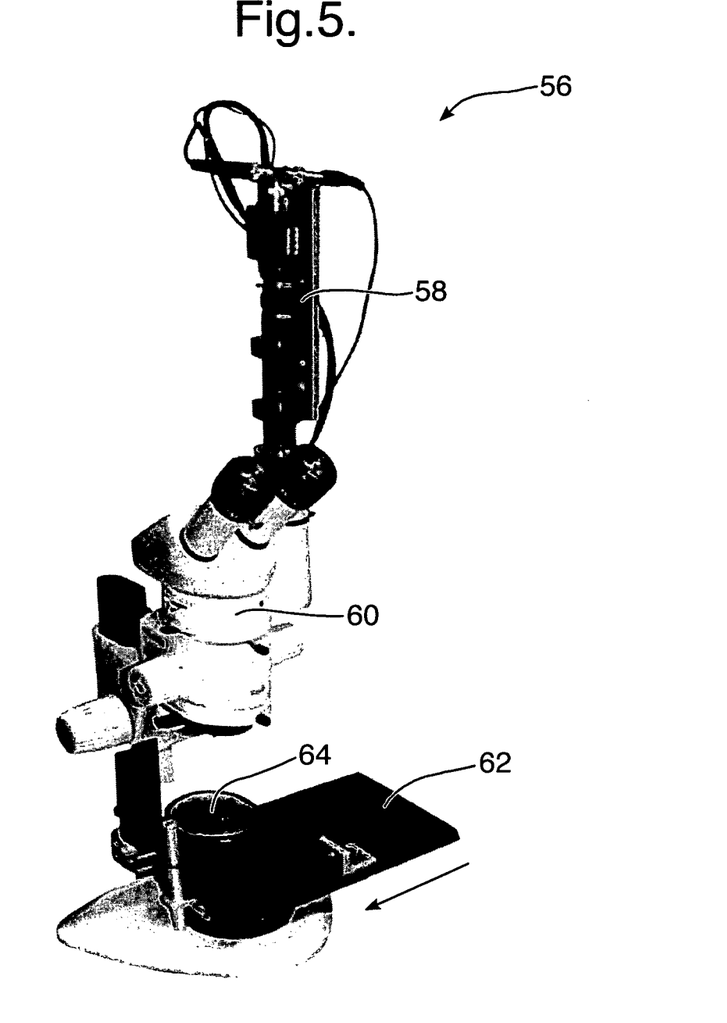
FIG. 5 is a perspective view of a hyperspectral microscopic imager in accordance with the invention.

FIG. 5 shows a hyperspectral microscopic imager 56 for use in the method mentioned above forming an embodiment of another part of the invention. The imager 56 comprises a microscope component 60, adapted from a conventional optical microscope, such as a Leitz Leca MS5 microscope (1-80x), and a hyperspectral imaging component 58, such as an Astrovid StellaCam II Video Camera [AV-STCA2] with a pixel array of 640×480, containing optics as described with reference to FIG. 1. The objective lens of the hyperspectral imaging component 58 may, by way of example, have a focal length of 25 mm and f:1.6.

The hyperspectral imaging component 58 has an image capture means; for example an ARCOS pocket video recorder AV400 capturing AVI video at 25 frames/sec. In one example, each video frame recorded (spectral profile), consists of the light spectrum from 363 to 685 nm dispersed over 640 pixels, giving a resolution of 0.5 nm/pixel. The spatial resolution perpendicular to the moving direction in this example is 193 pixels.

The imager 56 further comprises a moveable platform 62, which can be moved in the direction indicated by the arrow by a stepper motor located underneath the platform. By way of example, the stepper motor may have a gear exchange of 1:500 giving a speed of 2.59 mm/sec. The platform 62 carries a watertight sample container 64, such as a Petri dish, which can hold a specimen in a volume of liquid. The container 64 is also arranged to direct light through a specimen from beneath, for example by means of a mirror and a diffuser, when determining optical transmission characteristics of a specimen; or with a light source above for determining optical reflectance. The imager 56 also comprises one or more light sources directable onto the upper surface of a specimen, preferably from an off axis angle such as at 45 degree to the vertical. The same light source may be used for either transmissive or reflective analysis and may consist of a halogen or other light source directed appropriately through two fibre optic bundles. This light source can be used when determining the reflectance characteristics of a specimen. The objective lens of the microscope component 60 may be lowered into the fluid carried in the sample container 64, to mitigate any optical interference that might be caused due to the fluid-air and air-lens boundaries when the objective lens is located out of the fluid.

In use, a sample is placed in fluid; such as sea water, in the sample container 64. The stepper motor moves the platform 62 in the direction of the arrow while the hyperspectral imaging component 58 captures sequential spectral image strips across the specimen orthogonal to the direction of motion. These strips can be combined as explained above with reference to FIG. 1. In particular, processing may be performed using YaPlaySpecX software (Fred Sigemes, UNIS, cf. Sigemes et al. 2000 Applied Optics) to compose monochromatic images from an AVI video, forming an spectral image cube. Depending on the light source selected, two- dimensional images of either spectral transmittance or spectral reflectance of the specimen in the liquid can be generated at high magnification through use of the imager 56.

If desired, average spectral characteristics (with statistical information on e.g. error estimates) for an area of interest captured with the hyperspectral microscopic imager 56, can be found by averaging information from an image hypercube in the spectral direction. The average spectral characteristics measured for reflection, $E_r$(lamda) (mW/nm), or transmission, $E_t$(lamda) (mW/nm), may be adjusted for the halogen lamp (or other light source) radiant intensity spectrum for reflection, $E_{hr}$(lamda) (mW/nm), and for transmission, $E_{ht}$(lamda) (mW/nm), to give a comparable reflectance or transmittance spectrum with optical density. The dimensionless reflectance spectra is then $R(\lambda)=E_r$(lamda)$/E_{hr}$(lamda) and the dimensionless transmittance spectra is T(lamda)=Et (lamda)$/E_{ht}$(lamda).

Figure 6A:
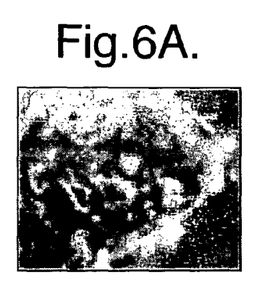
FIG. 6 shows the analysis of a specimen of a red alga using a magnifying hyperspectral imager in accordance with the invention.
Figure 6B:
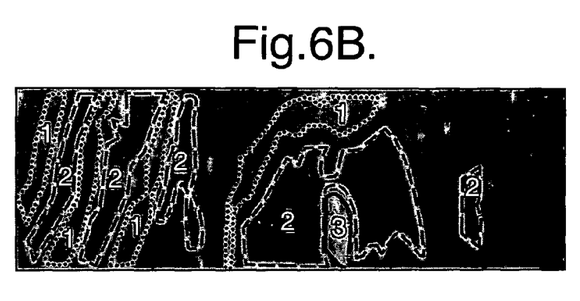
Figure 6C:
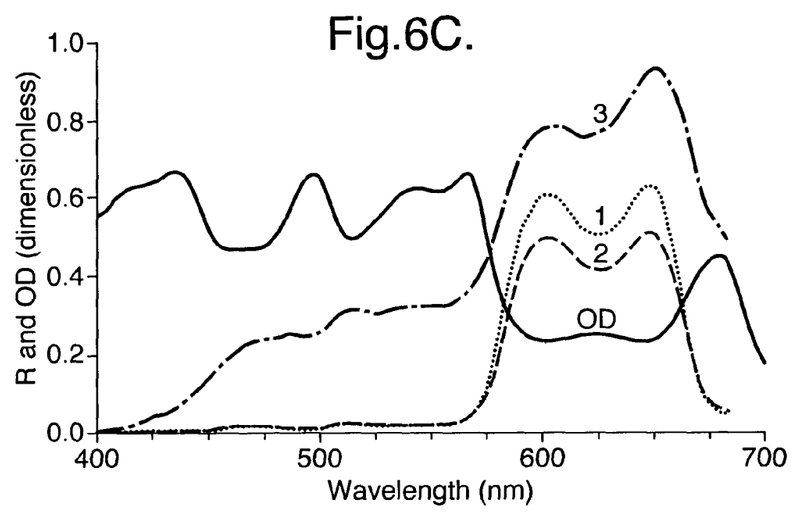

FIG. 6 shows an image A of a specimen of a red alga to be analysed using a magnifying hyperspectral imager in accordance with the invention. It also shows a magnified monochromatic image B of the specimen in water (at 600 nm wavelength) captured using the hyperspectral imager. Three distinct regions 1, 2, 3 are indicated, for which the average reflectance, R(lamda), over the region is to be determined. FIG. 6-C shows the R(lamda) spectra 1, 2, 3 obtained. It also shows the corresponding spectral absorbance spectrum OD, measured with a spectrophotometer, which validates the reflectance measurements (they should be inversely related). The reflectance measurements have been adjusted to compensate for the halogen lamp radiant intensity spectrum, $E_h(\lambda)$.

Once an averaged spectrum for a region of interest has been obtained, this can be used to identify other instances of the same material in other situations; in particular, it can be used with the apparatus described earlier to identify the same material underwater using in situ hyperspectral imaging apparatus.

The invention claimed is:

1. An apparatus for placement on or in a body of water for hyperspectral imaging of material in the water comprising an artificial light source and a hyperspectral imager which are arranged so that in use light exits the apparatus beneath the surface of the water and is reflected by said material before re-entering the apparatus beneath the surface of the water and entering said hyperspectral imager, wherein said hyperspectral imager is adapted to produce hyperspectral image data having at least two spatial dimensions, and wherein the apparatus is arranged to estimate a spectral attenuation coefficient of ambient water and to adjust a spectral output of the artificial light source so that a predetermined light spectrum arrives at said material.

2. An apparatus as claimed in claim 1 comprising one or more optical filters selectably placeable in the path of the light emitted from the artificial light source so as to adjust the spectral output of the artificial light source.

3. An apparatus as claimed in claim 2 comprising a plurality of optical filters selectably placeable in the path of the light emitted from the artificial light source, each having a unique spectral-filtering characteristic.

4. An apparatus as claimed in claim 1 wherein the artificial light source comprises a plurality of light-emitting elements each with differing emission spectra, the apparatus being arranged to supply power to the light-emitting elements, and wherein the apparatus is configured to alter the power supplied to respective light-emitting elements in order to give a required overall output spectrum.

5. An apparatus as claimed in claim 4 wherein the light-emitting elements comprise light emitting diodes.

6. An apparatus as claimed in claim 1 comprising an optical sensor and logic for estimating a spectral attenuation coefficient of the ambient water using an output from said optical sensor.

7. An apparatus as claimed in claim 1 wherein the hyperspectral imager operates using dispersive spectrography.

8. An apparatus as claimed in claim 1 wherein the hyperspectral imager has no independently moving parts.

9. An apparatus as claimed in any claim 1 arranged so that movement of the apparatus through the body of water enables an area of interest to be continuously imaged.

10. An apparatus as claimed in claim 1 comprising a tether for connecting to a ship or other vessel.

11. An apparatus as claimed in claim 10 wherein the tether comprises an umbilical power supply.

12. An apparatus as claimed in claim 1 comprising a portable power supply and wherein the apparatus is capable of independent movement.

13. An apparatus as claimed in claim 12 wherein the portable power supply comprises a battery.

14. An apparatus as claimed in claim 1 further comprising an image capturer for capturing frames from the hyperspectral imager.

15. An apparatus as claimed in claim 14 further comprising image processing logic arranged to process captured images from the hyperspectral imager.

16. An apparatus as claimed in claim 1 adapted to be fully submersible.

17. An apparatus as claimed in claim 16 comprising a housing designed to withstand external pressures of at least 10 bars.

18. An apparatus as claimed in claim 1 wherein the hyperspectral imager is arranged to provide a spectral resolution of finer than 1 nm.

19. An apparatus as claimed in claim 1 wherein the hyperspectral imager is arranged to image over the whole spectrum of visible light.

20. An apparatus as claimed in claim 1 wherein the hyperspectral imager has a maximum physical dimension of less than 50 cm.

21. An apparatus as claimed in claim 1 wherein the hyperspectral imager weighs less than 1 kg.

22. An apparatus as claimed in claim 1 wherein the hyperspectral imager consumes less than 2 Watts.

23. A method of imaging material beneath the surface of a body of water comprising:
    illuminating said material with an artificial light source from beneath the surface of the water;
    receiving from beneath the surface of the water light reflected from said material into a hyperspectral imager;
    said hyperspectral imager generating hyperspectral image data from said material, said image data having at least two spatial dimensions;
    estimating a spectral attenuation coefficient of ambient water; and
    adjusting a spectral output of the artificial light source so that a predetermined light spectrum arrives at said material.

24. A method as claimed in claim 23 wherein the artificial light source is provided in the same unit as the imager.

25. A method as claimed in claim 23 comprising use of apparatus for placement on or in a body of water for hyperspectral imaging of material in the water, comprising an artificial light source and a hyperspectral imager which are arranged so that in use light exits the apparatus beneath the surface of the water and is reflected by said material before re-entering the apparatus beneath the surface of the water and entering said hyperspectral imager, wherein said hyperspectral imager is adapted to produce hyperspectral image data having at least two spatial dimensions, and wherein the apparatus is arranged to estimate a spectral attenuation coefficient of the ambient water and to adjust the spectral output of the artificial light source so that a predetermined light spectrum arrives at said material.

26. A method as claimed in claim 23 comprising the further step of using the hyperspectral imager to determine whether a predetermined spectrum for the artificial light is achieved.

27. A method as claimed in claim 23 comprising the further step of using an optical sensor to determine whether a predetermined spectrum for the artificial light is achieved.

28. A method as claimed in claim 23 wherein said estimating is continuous.

29. A method as claimed in claim 23 comprising the further step of locating a spectral filter in the path of the artificial light.

30. A method as claimed in claim 23 comprising the further step of selectively illuminating elements from among a set of spectrally-distinct light-emitting elements.

31. A method as claimed in claim 23 wherein the predetermined light spectrum comprises substantially uniform energy across the visible spectrum.

32. A method as claimed in claim 23 further comprising:
    deploying a calibration surface having known reflectance characteristics; and
    using feedback control to alter the spectrum of light emitted by the artificial light source depending on the spectrum of the light reflected from the calibration surface until a predetermined spectrum for the reflected light is achieved.

33. A method as claimed in claim 32 wherein the calibration surface is a white polytetrafluoroethylene disc and wherein the disc is deployed in front of the hyperspectral imager at a given distance.

34. A method as claimed in claim 23 comprising the further step of locating or mapping the extent of one or more organisms or other material by the characteristic spectral fingerprint(s) thereof.

35. An apparatus for placement on or in a body of water for hyperspectral imaging of material in the water comprising an artificial light source and a hyperspectral imager which are arranged so that in use light exits the apparatus beneath the surface of the water and is reflected by said material before re-entering the apparatus beneath the surface of the water and entering said hyperspectral imager, wherein said hyperspectral imager is adapted to produce hyperspectral image data having at least two spatial dimensions, and wherein the apparatus is arranged to estimate a spectral attenuation coefficient of ambient water and to compensate for the attenuation of reflected or emitted light returning to the apparatus.

36. A method of imaging material beneath the surface of a body of water comprising:
    illuminating said material with an artificial light source from beneath the surface of the water;
    receiving from beneath the surface of the water light reflected from said material into a hyperspectral imager;
    said hyperspectral imager generating hyperspectral image data from said material, said image data having at least two spatial dimensions;
    estimating a spectral attenuation coefficient of ambient water; and
    compensating for the attenuation of reflected or emitted light returning to the apparatus.

* * * * *